(12) United States Patent
Miller et al.

(10) Patent No.: US 7,799,031 B2
(45) Date of Patent: Sep. 21, 2010

(54) REDUCING INSTRUMENT FOR SPINAL SURGERY

(75) Inventors: Keith E. Miller, Germantown, TN (US); Alan Rezach, Atoka, TN (US); Greg Denzer, Memphis, TN (US); Christopher Shaffrey, Charlottesville, VA (US); Marcel Dvorak, Vancouver (CA); Charles Fisher, Vancouver (CA); Jeff Wang, Sherman Oaks, CA (US); Ricardo C. Sasso, Carmel, IN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 640 days.

(21) Appl. No.: 11/701,979

(22) Filed: Feb. 2, 2007

(65) Prior Publication Data
US 2007/0276379 A1    Nov. 29, 2007

Related U.S. Application Data

(63) Continuation of application No. 11/449,110, filed on Jun. 8, 2006, now abandoned, which is a continuation of application No. 11/255,508, filed on Oct. 21, 2005, now abandoned, which is a continuation of application No. 11/054,044, filed on Feb. 9, 2005, now abandoned.

(51) Int. Cl.
*A61F 5/00* (2006.01)

(52) U.S. Cl. ..................... 606/86 A; 606/279

(58) Field of Classification Search .............. 606/86 A, 606/86 R, 99–103, 104–105, 246, 279, 53, 606/96–98

See application file for complete search history.

(56) References Cited

U.S. PATENT DOCUMENTS

| | | | |
|---|---|---|---|
| 5,020,519 A * | 6/1991 | Hayes et al. | 606/237 |
| 5,616,143 A * | 4/1997 | Schlapfer et al. | 606/86 A |
| 5,720,751 A * | 2/1998 | Jackson | 606/86 R |
| 5,910,141 A * | 6/1999 | Morrison et al. | 606/86 A |
| 6,726,692 B2 * | 4/2004 | Bette | 606/99 |
| 6,746,449 B2 * | 6/2004 | Jones et al. | 606/86 A |
| 7,371,239 B2 * | 5/2008 | Dec et al. | 606/279 |
| 7,470,279 B2 * | 12/2008 | Jackson | 606/300 |
| 2002/0095153 A1 * | 7/2002 | Jones et al. | 606/61 |
| 2003/0229347 A1 * | 12/2003 | Sherman et al. | 606/61 |
| 2004/0267275 A1 * | 12/2004 | Cournoyer et al. | 606/99 |
| 2005/0059969 A1 * | 3/2005 | McKinley | 606/61 |
| 2005/0171540 A1 * | 8/2005 | Lim et al. | 606/61 |
| 2005/0192570 A1 * | 9/2005 | Jackson | 606/61 |

(Continued)

OTHER PUBLICATIONS

"hole." Merriam-Webster Online Dictionary. 2009.Merriam-Webster Online. Dec. 8, 2009<http://www.merriam-webster.com/dictionary/hole>.*

*Primary Examiner*—Eduardo C Robert
*Assistant Examiner*—Steven J Cotroneo

(57) ABSTRACT

An instrument is provided for reduction of a rod or other elongated member into an implant, such as a bone screw. In one embodiment, such an instrument includes a rod adjusting assembly pivotably attached to an implant holding assembly. The implant holding assembly can be pivotably connected to an implant, and the rod adjusting assembly is operable to move a rod toward or away from the implant holding assembly. In that embodiment, several motions are possible by the instrument so that relatively small or large movements of a rod with respect to an implant may be made.

29 Claims, 13 Drawing Sheets

U.S. PATENT DOCUMENTS

2005/0192579 A1* 9/2005 Jackson ................ 606/72
2006/0111730 A1* 5/2006 Hay .................... 606/104
2006/0229614 A1* 10/2006 Foley et al. ............ 606/61
2008/0228233 A1* 9/2008 Hoffman et al. ......... 606/86 A
2008/0312703 A1* 12/2008 Hestad et al. .......... 606/86 A

* cited by examiner

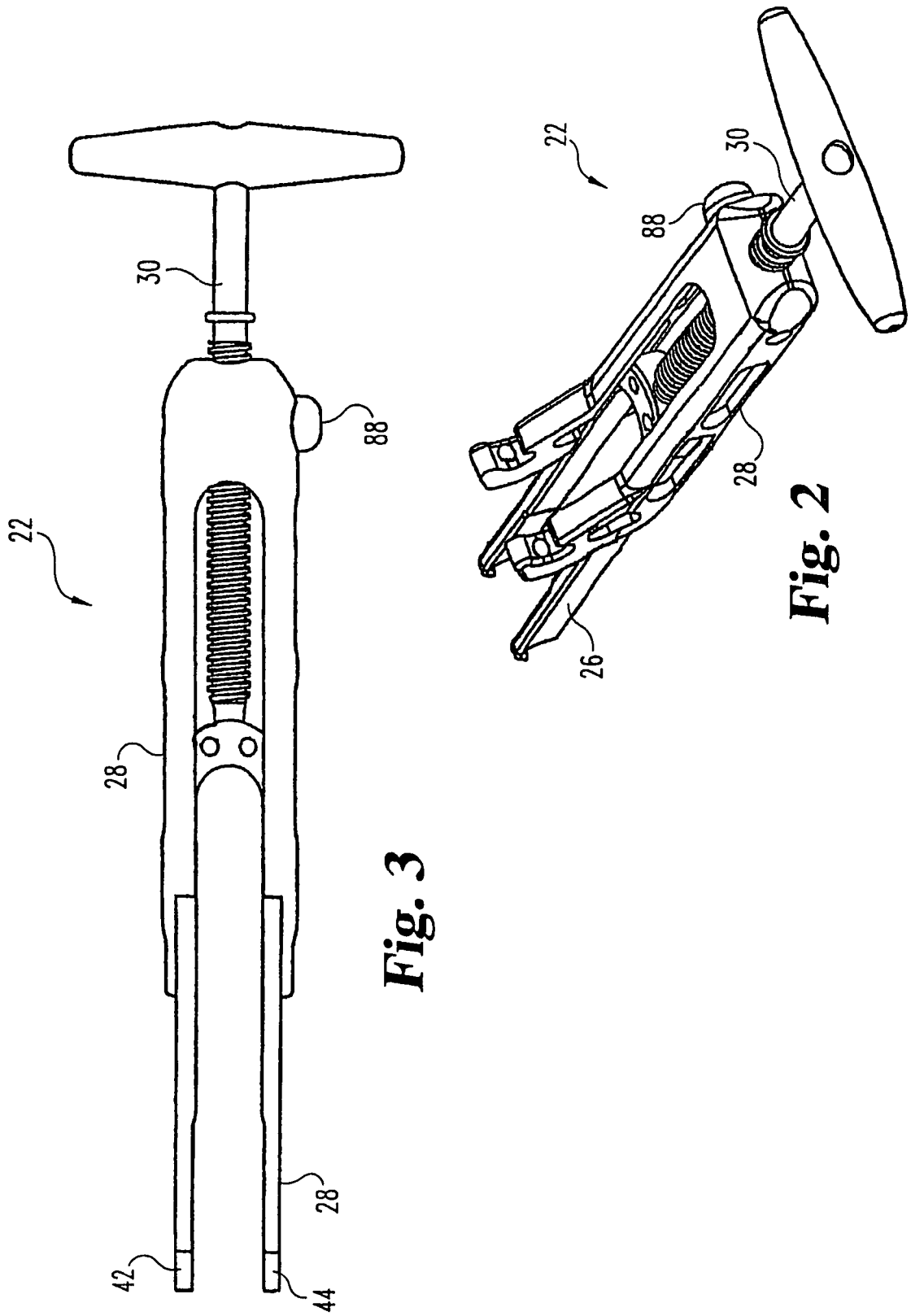

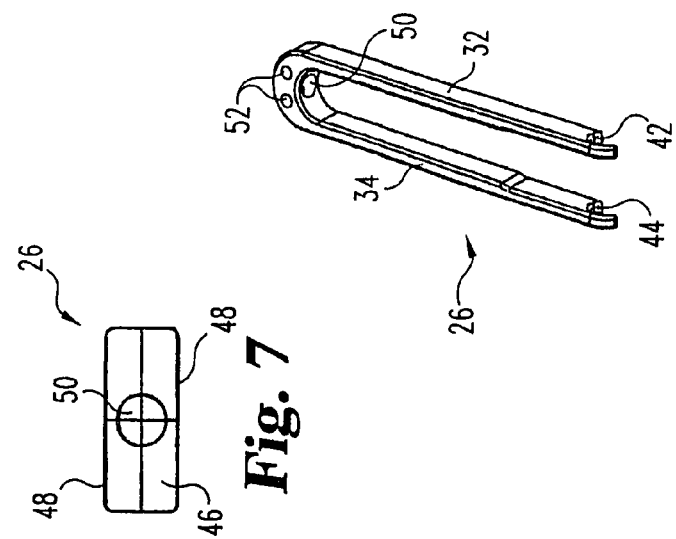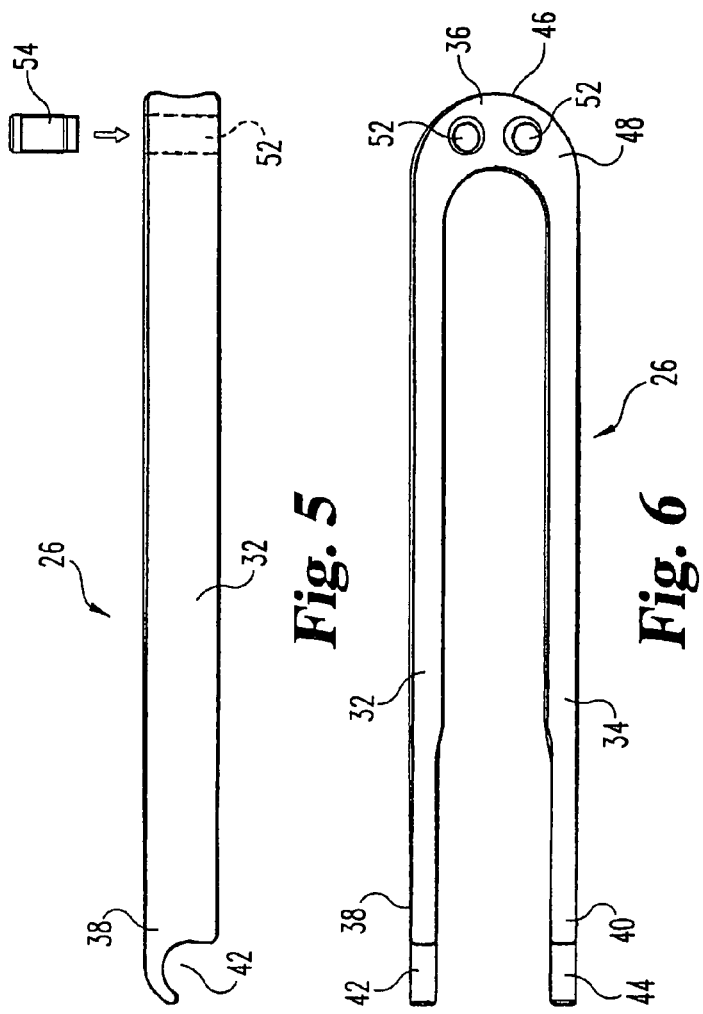

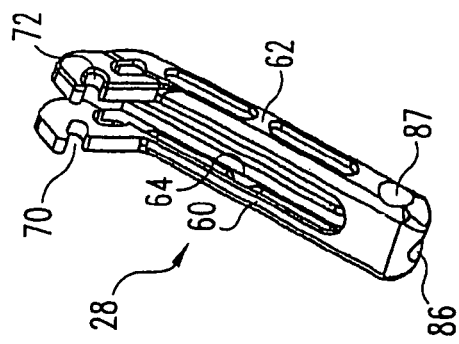
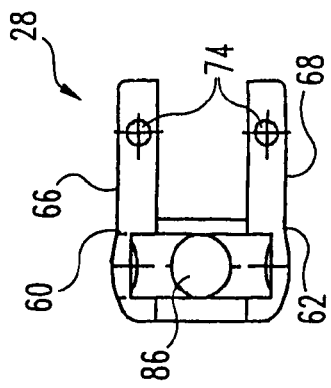
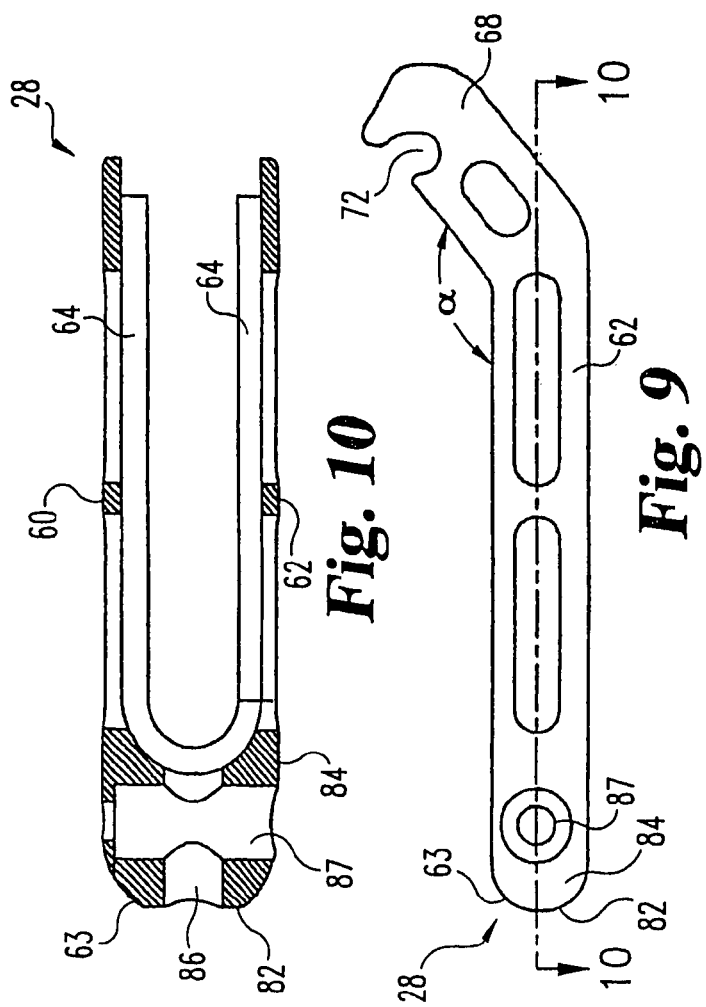
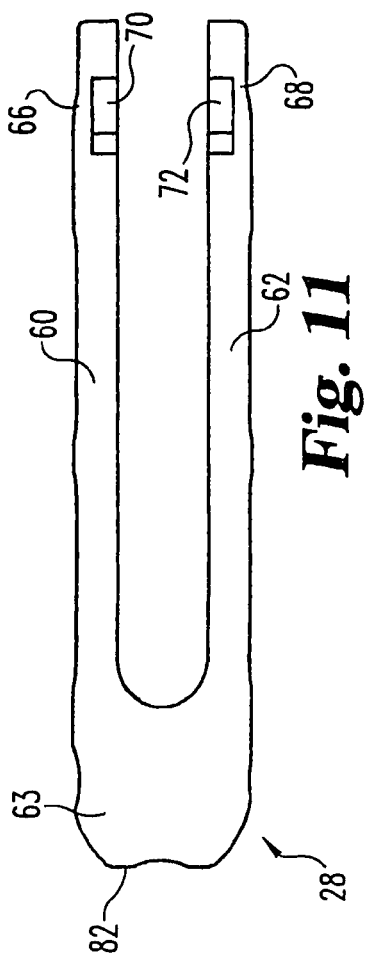

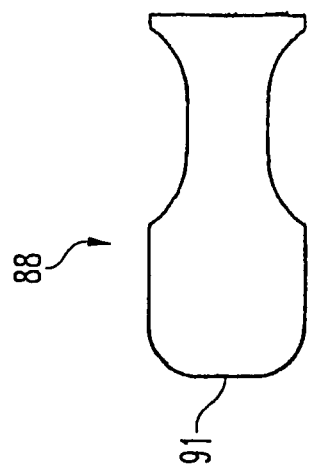
Fig. 17
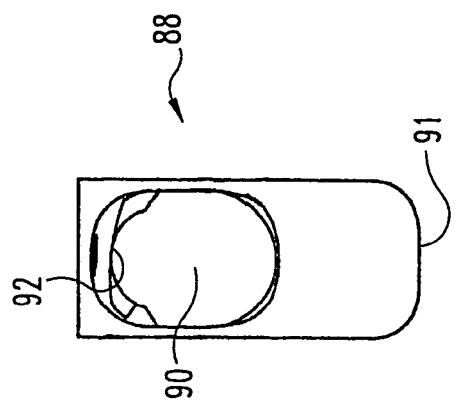
Fig. 14
Fig. 15
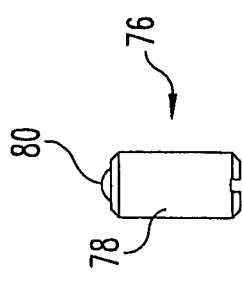
Fig. 13
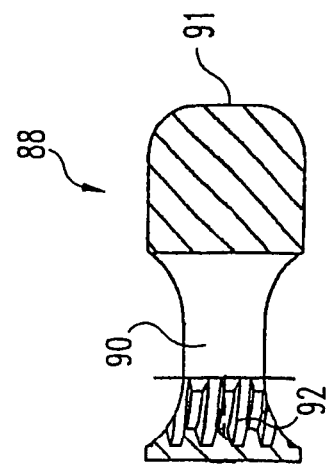
Fig. 16

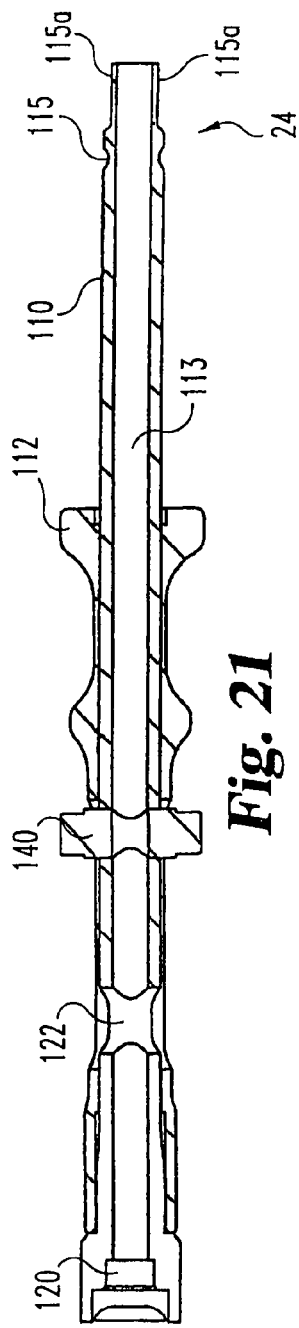
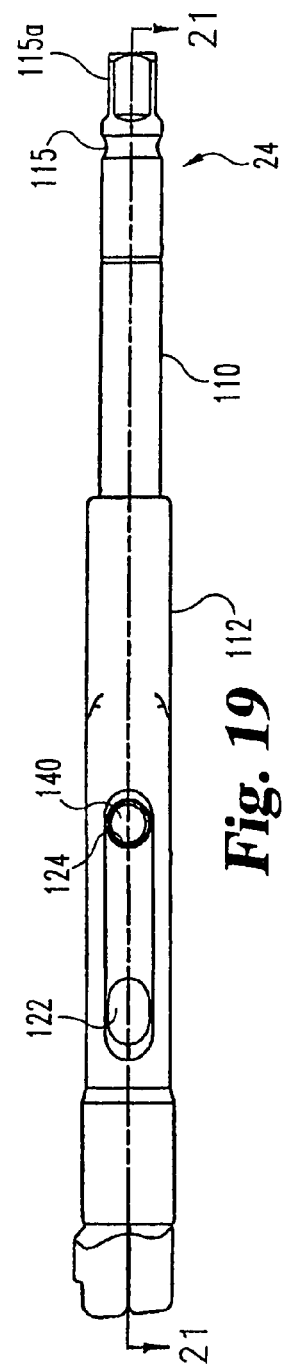
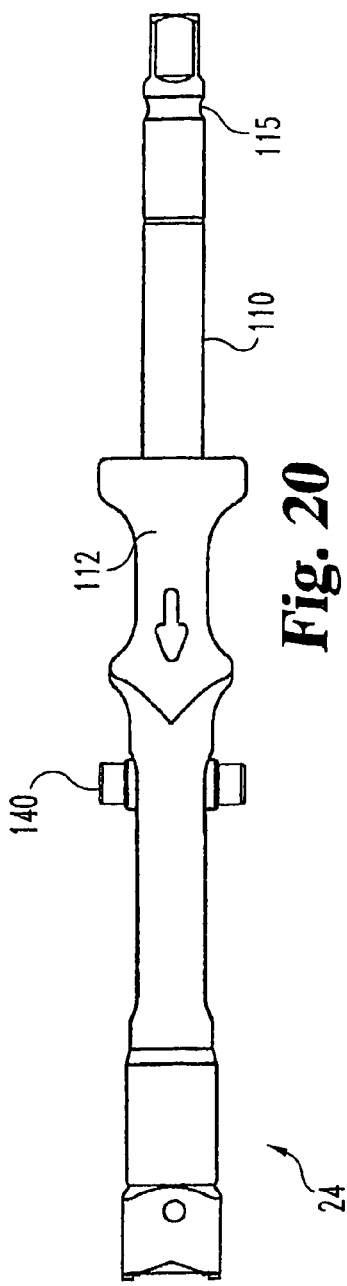
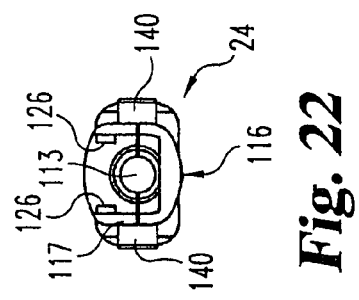

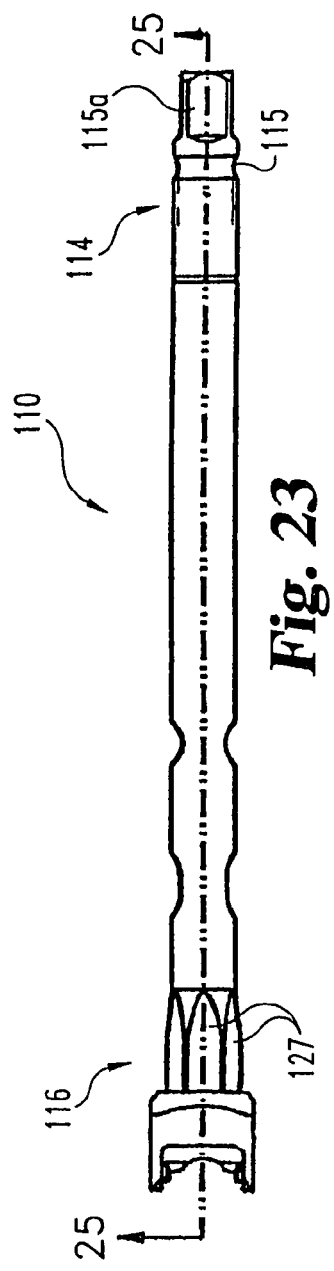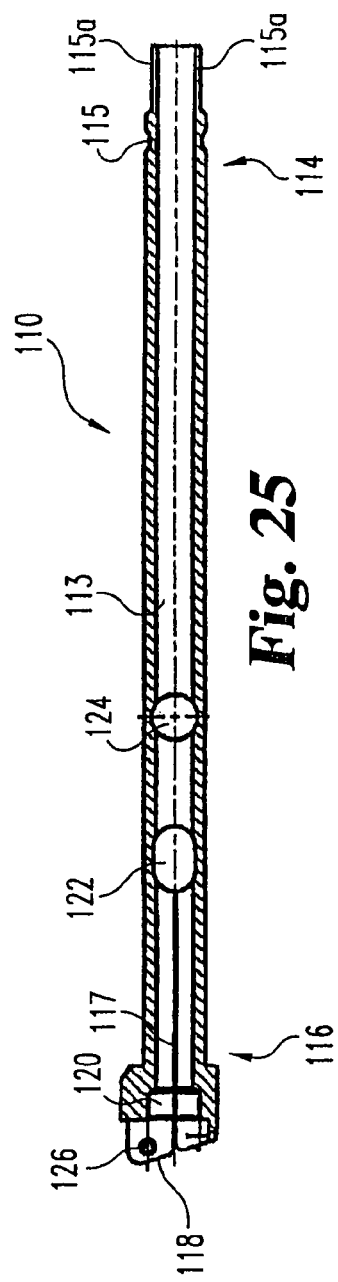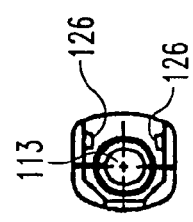

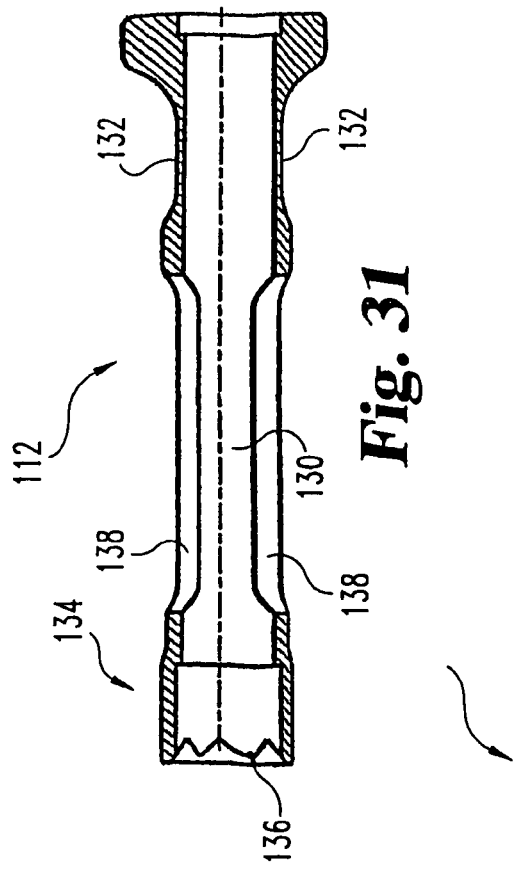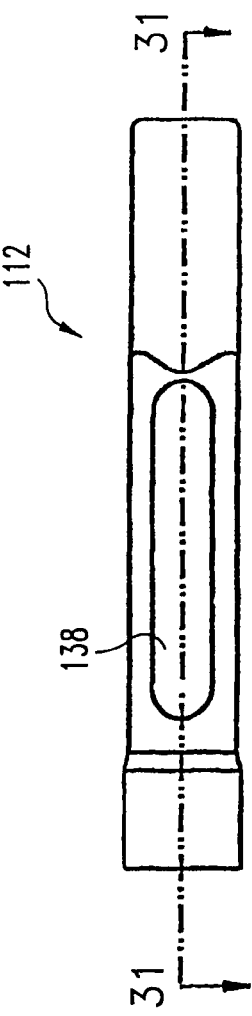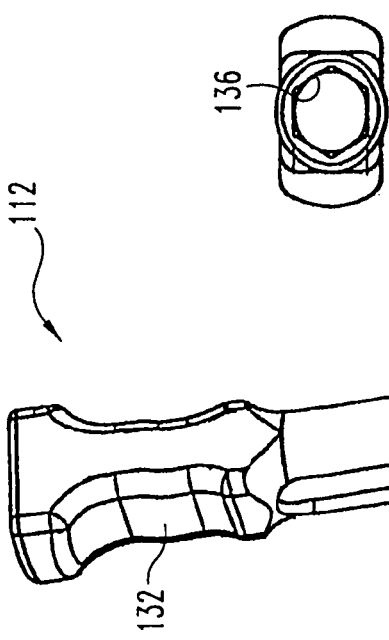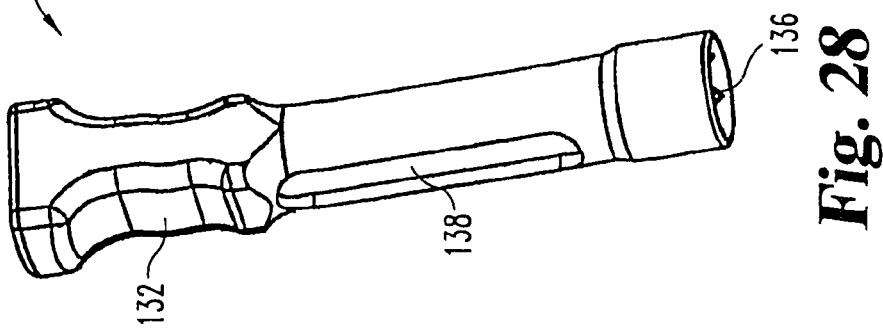

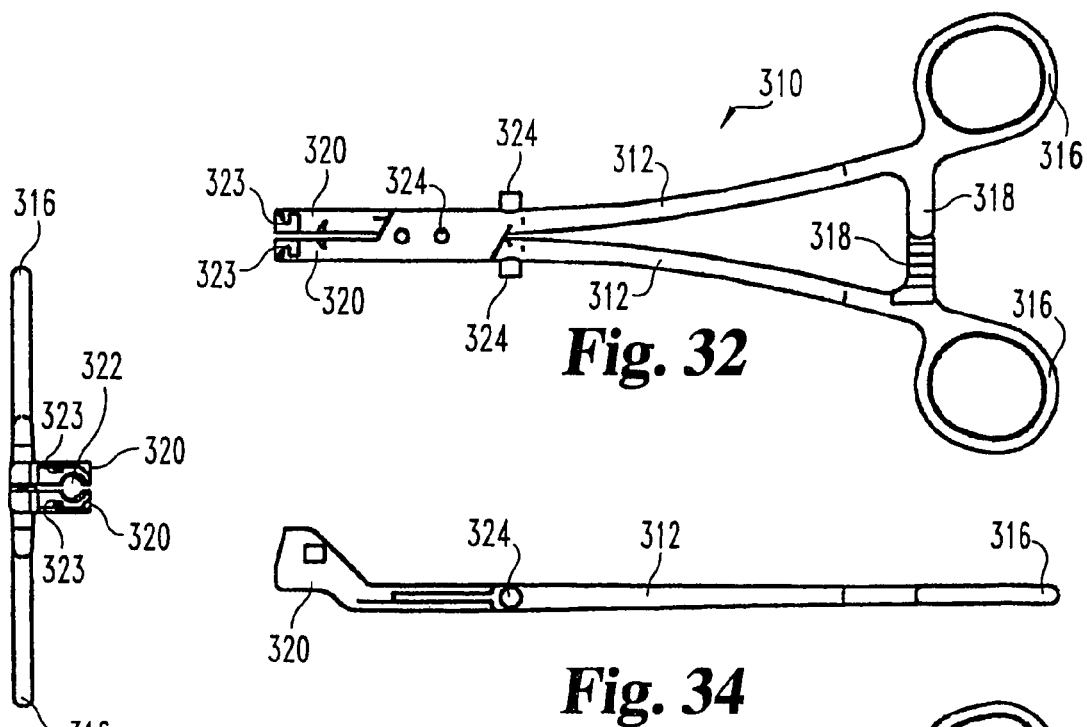
Fig. 32
Fig. 33
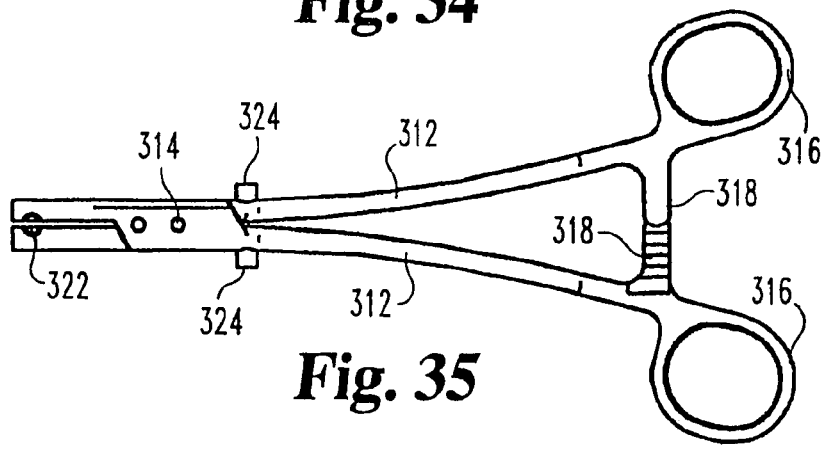
Fig. 34
Fig. 35

REDUCING INSTRUMENT FOR SPINAL SURGERY

The present application is a continuation of application Ser. No. 11/449,110, filed Jun. 8, 2006 now abandoned which is a continuation of application Ser. No. 11/255,508, filed Oct. 21, 2005 now abandoned which is a continuation of application Ser. No. 11/054,044, filed on Feb. 9, 2005, now abandoned which applications are incorporated herein by reference in their entirety.

BACKGROUND

In orthopedic surgical procedures, it is known to implant devices to support bones or other tissue, to correct deformities, to hold tissues in position for healing after injuries or other surgery, and for other purposes relating to orthopedic health. For example, where correction of a scoliotic or other abnormal curvature or misalignment of the spine is desired, a sturdy rod, plate, or other elongated connecting member can be placed along one or more vertebral segments to support or hold the segments in a corrected position. Bone screws, bone hooks or other fixation implants are attached to vertebrae and connected to the connecting member to secure the connecting member along the spinal column.

Commonly, the fixation implants and the connecting member(s) are placed separately, that is, they are not connected together prior to implantation in the body. For example, bone screws may be implanted into vertebrae first, connectors may be placed on or around the screws (if necessary), and then the connecting member may be placed into the body. The connecting member may be contoured prior to insertion to approximate the curvature desired, or it may be contoured after placement adjacent the spine. In cases where a connecting member and bone screws or other fixation elements are separately placed, the connecting member and screws may be required to be forced toward each other for connection. The process of moving the connecting member and fixation elements toward each other for connection is generally termed "reduction."

Reduction can be accomplished by hand, although the environment and close quarters of a surgical site can make reduction by hand quite difficult. While instruments have been developed to provide a mechanical advantage in reducing or positioning the connecting member relative to an anchor, there remains a need for reducing instruments which are maneuverable relative to the anchor and connecting member to facilitate insertion and manipulation of the connecting member and anchor through the incision or portal in which the reducing instrument is positioned.

BRIEF DESCRIPTION OF THE DRAWINGS

FIG. 2 is a perspective view of an embodiment of one aspect of an instrument for reducing a rod into an orthopedic implant.

FIG. 3 is a side view of the structure shown in FIG. 2.

FIG. 4 is a perspective view of an embodiment of one aspect of the structure shown in FIG. 2.

FIG. 5 is a side view of the structure shown in FIG. 4.

FIG. 6 is a side view, rotated ninety degrees from the view shown in FIG. 5, of the structure shown in FIG. 4.

FIG. 7 is a top view of the structure shown in FIG. 4.

FIG. 8 is a perspective view of an embodiment of another aspect of the structure shown in FIG. 2.

FIG. 9 is a side view of the structure shown in FIG. 8.

FIG. 10 is a cross-sectional view of the structure shown in FIG. 9, taken along the line 10-10 in FIG. 9 and viewed in the direction of the arrows.

FIG. 11 is a side view, rotated ninety degrees from the view shown in FIG. 9, of the structure shown in FIG. 8.

FIG. 12 is a bottom view of the structure shown in FIG. 8.

FIG. 13 is a side view of an embodiment of a plunger that may be used in the embodiments shown in FIGS. 1 and 2.

FIG. 14 is a top view of an embodiment of a button that may be used in the embodiments shown in FIGS. 1 and 2.

FIG. 15 is a side view of the embodiment shown in FIG. 14.

FIG. 16 is a cross-sectional view of the embodiment shown in FIG. 14, taken along the lines 16-16 in FIG. 15 and viewed in the direction of the arrows.

FIG. 17 is a side view of the embodiment shown in FIG. 14.

FIG. 19 is a side view of an embodiment of another aspect of the embodiment shown in FIG. 1.

FIG. 20 is a side view, rotated ninety degrees from the view in FIG. 19, of the structure shown in FIG. 19.

FIG. 21 is a cross-sectional view of the structure shown in FIG. 19, taken along the lines 21-21 and viewed in the direction of the arrows.

FIG. 22 is an end view of the structure shown in FIG. 19.

FIG. 23 is a side view of an embodiment of another aspect of the embodiment shown in FIG. 1.

FIG. 24 is an end view of the structure shown in FIG. 23.

FIG. 25 is a cross-sectional view of the structure shown in FIG. 23, taken along the lines 25-25 in FIG. 23 and viewed in the direction of the arrows.

FIG. 28 is a perspective view of an embodiment of another aspect of the embodiment shown in FIG. 1

FIG. 29 is an end view of the structure shown in FIG. 28.

FIG. 30 is a side view of the structure shown in FIG. 28.

FIG. 31 is a cross-sectional view of the structure shown in FIG. 30, taken along the lines 31-31 and viewed in the direction of the arrows.

FIG. 32 is a top view of an alternative embodiment of a device that can be used to connect to an implant.

FIG. 33 is an end view of the embodiment shown in FIG. 32.

FIG. 34 is a side view of the embodiment shown in FIG. 32.

FIG. 35 is a bottom view of the embodiment shown in FIG. 32.

DESCRIPTION OF THE ILLUSTRATED EMBODIMENT

Figure 1:
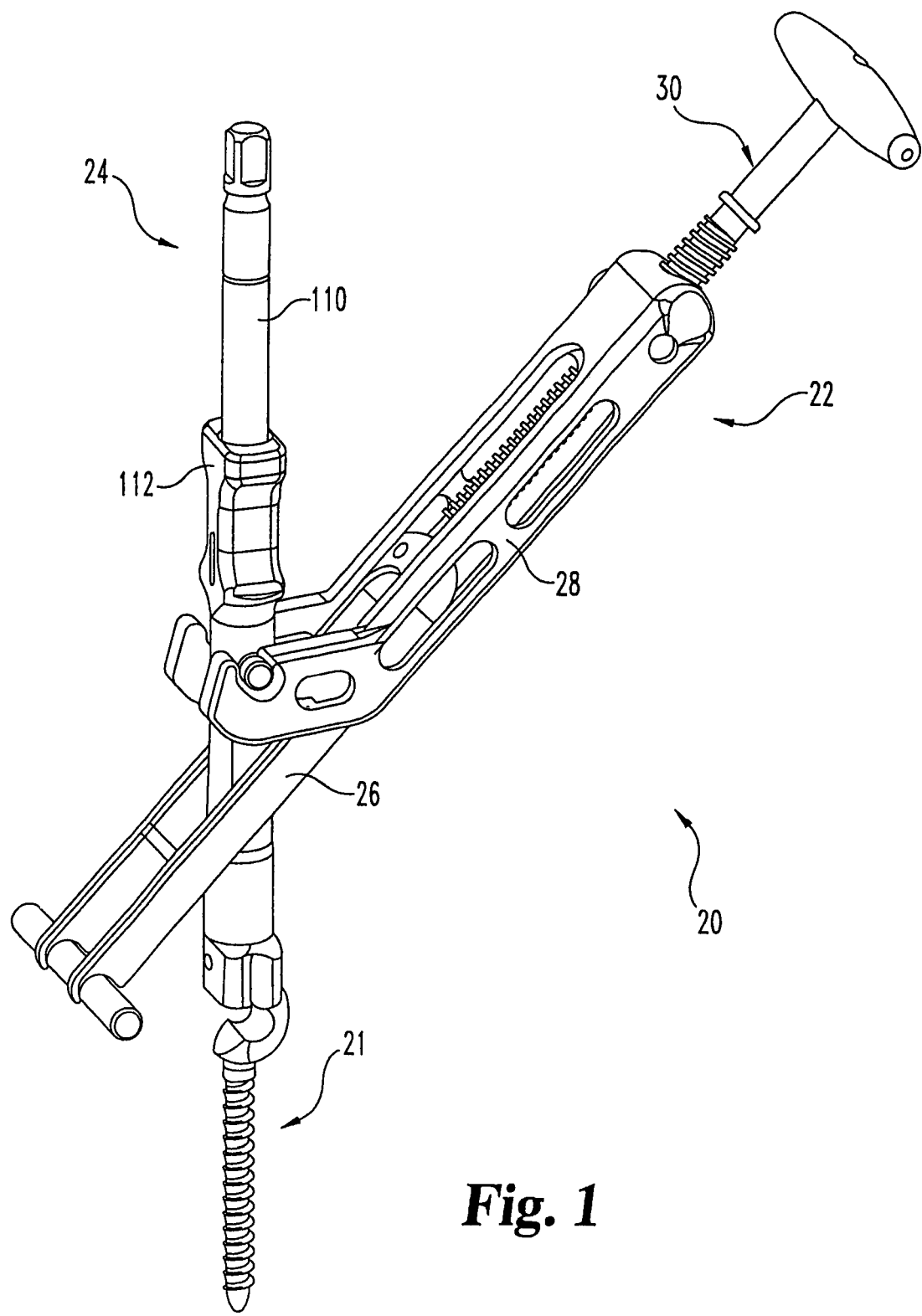
FIG. 1 is a perspective view of an embodiment of an instrument for reducing a rod into an orthopedic implant.
Figure 18:
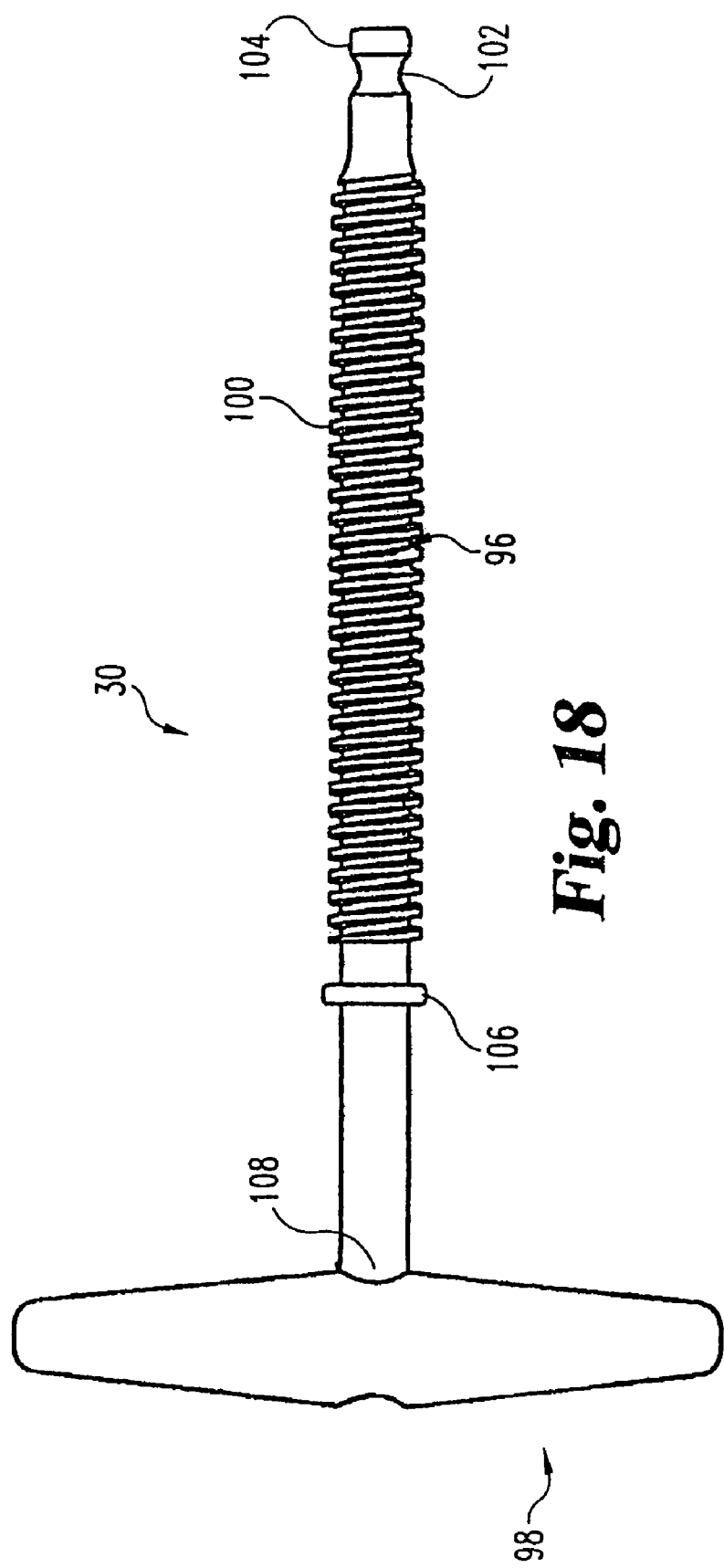
FIG. 18 is a side view of an embodiment of an adjusting mechanism that may be used in the embodiments shown in FIGS. 1 and 2.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated device, and any such further applications of the principles of the invention as illustrated herein, are contemplated as would normally occur to one skilled in the art to which the invention relates.

An embodiment of a rod reducing instrument 20 connected to a side-loading bone screw 21 is shown in FIG. 1. That embodiment of instrument 20 includes a rod adjusting assembly 22 and an implant holding assembly 24. Rod adjusting assembly 22 and implant holding assembly 24 are generally pivotable with respect to each other, in order to assist in inserting a rod or other elongated orthopedic member into a bone screw or other implant, as further described below.

Assembly 22 includes a reducer portion 26, a sleeve or slider portion 28, and an adjustment mechanism 30. As indicated from the drawings of this embodiment, reducer portion 26 is slidably connected to an inner portion of sleeve 28. Adjustment mechanism 30 fits through sleeve 28 and connects to reducer portion 26, so that activating adjustment mechanism 30 moves reducer portion 26 with respect to sleeve 28.

Reducer portion 26 is substantially U-shaped, having two leg portions 32 and 34 that are substantially parallel to each other, and a cross piece 36. Leg portions 32 and 34 have respective end portions 38 and 40 that are distal from cross piece 36. End portion 38 has a hollow 42 formed in it, at least some of which in a particular embodiment is substantially cylindrical and may include an arc of about 150 to 180 degrees. Similarly, end portion 40 has a hollow 44 formed in it, at least some of which in a particular embodiment is substantially cylindrical and may include an arc of about 150 to 180 degrees. Hollows 42 and 44 may be essentially aligned, and sized and configured to accommodate an orthopedic rod, e.g. cylindrical parts of hollows 42 and 44 may have axes that are substantially collinear. Leg portions 32 and 34 may be substantially linear, or they may include an angle between cross piece 36 and hollows 42 and 44. In the latter case, the angles in leg portions 32 and 34 may be substantially equal, so that upper parts of legs 32 and 34 (e.g. those proximate to cross piece 36) are coplanar in a first plane, and lower parts of legs 32 and 34 (e.g. those proximate to hollows 42 and 44) are coplanar in a second plane that is angled with respect to the first plane.

Cross piece 36 includes an upper surface 46 and a side surface 48. An aperture 50 may be drilled or otherwise formed into or through upper surface 46 to accommodate adjustment mechanism 30, as further described below. One or more holes 52 may be drilled or otherwise formed into or through side surface 48 of cross piece 36, and holes 52 intersect aperture 50. Pins 54 are inserted into holes 52 to retain adjustment mechanism 30 in aperture 50, as further discussed below.

Sleeve or slider portion 28, in one embodiment, is substantially U-shaped, having leg portions 60 and 62, and cross piece 63. Leg portions 60 and 62 are substantially identical in the illustrated embodiment. Internal sides of leg portions 60 and 62 each include a groove 64 sized to accommodate at least a portion of the leg portions 32 and 34 of reducer portion 26. Leg portions 60 and 62 of sleeve 28 have respective end portions 66 and 68. End portion 66 has a hollow 70 formed in it, at least some of which in a particular embodiment is substantially cylindrical and may include an arc of about 180 degrees. Similarly, end portion 68 has a hollow 72 formed in it, at least some of which in a particular embodiment is substantially cylindrical and may include an arc of about 180 degrees. Hollows 70 and 72 may be essentially aligned and sized to connect to a part of implant holding assembly 24, e.g. cylindrical parts of hollows 70 and 72 may have axes that are substantially collinear. In a particular embodiment, a hole 74 may be formed in one or both leg portions 60 and 62, within hollows 70 and 72. In hole(s) 74 a plunger 76 having a biased ball may be placed. Plunger 76 includes casing 78 within which is a spring (not shown) and a ball 80 above the spring, so that a portion of ball 80 extends outside casing 78. Plunger(s) 76 can assist to create a more secure connection between rod adjusting assembly 22 and implant holding assembly 24. It will be seen that other mechanisms for improving contact between rod adjusting assembly 22 and implant holding assembly 24 may be used, including snap-fit sizing, spring-loaded clips, or the like.

Leg portions 60 and 62 may be substantially linear, or they may include an angle between cross piece 63 and hollows 70 and 72. In the latter case, the angles in leg portions 60 and 62 may be substantially equal, so that upper parts of legs 60 and 62 (e.g. those proximate to cross piece 63) are coplanar in a first plane, and lower parts of legs 60 and 62 (e.g. those proximate to hollows 70 and 72) are coplanar in a second plane that is angled with respect to the first plane. An angle α between such upper and lower parts may be approximately 135 degrees.

Cross piece 63 includes an upper surface 82. A side surface 84 is provided that may be part of cross piece 63, leg portion 60, or both. Upper surface 82 has an aperture 86 therethrough for accommodating a part of adjustment mechanism 30, as further described below. Side surface 84 includes a hole 87 that is substantially perpendicular, in one embodiment, to aperture 86, and hole 87 intersects aperture 86. Within hole 87 is placed a button 88 and a spring (not shown), so that button 88 is biased outwardly, i.e. button 88 may be pressed in toward cross piece 63 against the bias of the spring. Button 88 is substantially cylindrical, having an oblong opening 90 therethrough. The long dimension of opening 90 is somewhat larger than an outer dimension of a shaft part of adjustment mechanism 30. Button 88 has a contact surface 91 that extends outside of sleeve 28 against which a surgeon can push. Opening 90 is partially threaded at a portion 92 distal from contact surface 91. Threaded portion 92 has a thread configuration that is compatible with a shaft part of adjustment mechanism 30.

Adjustment mechanism 30 includes a shaft portion 96 and a handle portion 98. Shaft portion 96 includes thread or threads 100 along at least a part. Shaft portion 98 further has a groove 102 adjacent to a distal end 104. In the illustrated embodiment, thread(s) 100 terminate above groove 102. At or above an upper end of thread(s) 100, a collar or boss 106 is provided, which may be integral with, fixedly attached to, or otherwise connected to shaft 96. Handle portion 98 is fixed or connected to shaft 96 at or adjacent to a proximal end 108 of shaft 96.

Shaft portion 96 extends through aperture 86 of cross piece 63, and through opening 90 of button 88. In one embodiment, the major diameter of thread(s) 100 is slightly smaller than a minimum dimension of aperture 86 so that shaft portion 96 can rotate without substantial hindrance in aperture 86. Collar 106 is slightly larger than aperture 86, in a particular embodiment, so that collar 106 prevents shaft portion 96 from moving through aperture 86 more than a desired amount. When button 88 is not being pushed in, it is biased so that threaded portion 92 engages thread 100 of shaft portion 96. Button 88 thus allows shaft 96 to be rotated and advance along threads 92 and 100, but does not allow direct translation of shaft 96 through aperture 86 and opening 90, i.e. shaft 96 cannot move through aperture 86 and opening 90 without rotating shaft 96.

Shaft portion 96 extends between leg portions 60 and 62 and into aperture 50 of cross piece 36 of reducer portion 26. Groove 102 is within aperture 50 and adjacent holes 52 in cross piece 36. Pin(s) 54 are inserted in holes 52 and into a portion of groove 102, adjacent to or abutting with shaft portion 96. In this embodiment, shaft 96 is thus rotatable with respect to reducer portion 26, but cannot be removed from cross piece 36 of reducer portion 26 without removal of pin(s) 54. Turning handle 98 of adjustment mechanism 30 causes shaft 96 to rotate and move out of or into sleeve 28, which causes reducer portion 26 to move toward or away from cross piece 63 of sleeve 28. When button 88 is pushed in, shaft 96 can be directly pushed into or pulled out of sleeve 28, with the like motion of reducer portion 26 with respect to sleeve 28.

Implant holding assembly 24 includes an internal piece 110 and an external piece 112, which in one embodiment are translatable along a common axis with respect to each other. Internal piece 110 is substantially cylindrical with a central lumen 113 in the illustrated embodiment, a proximal portion 114 and a distal portion 116. Proximal portion 114 may include a gripping surface roughened as by knurling or other process, and/or an end having a square, hexagonal or other configuration for accommodating a tool for holding or manipulating internal piece 110. A groove 115 and flats 115a may be provided in proximal portion 114, which can be used to connect to or accommodate other tools. Distal portion 116 may be slotted or open to allow connection of distal portion 116 to a bone screw or other implant into which a rod or elongated member is to be placed, without impeding the channel or other area in the implant where the rod is to rest. For example, a slot 117 may bifurcate distal end 116 so that distal end 116 may be somewhat elastically expandable. Distal end 116 may also have a surface 118 that is obliquely angled to a longitudinal axis of internal piece 110. Distal end 116 may be somewhat wider than other parts or the remainder of internal piece 110. In one embodiment, a chamber 120 may be formed in or proximate to distal end 116 and concentric with and communicating with lumen 113. One or more holes, e.g. holes 122 and 124, may be formed in internal piece 110. In the illustrated embodiment, such hole(s) are generally perpendicular to lumen 113. Hole 122 is substantially oval, and hole 124 is substantially circular.

Distal portion 116, in one embodiment, includes one or more protrusions 126 that are sized and/or shaped to fit into slots or openings on the side of the implant (e.g. implant 21). In the illustrated embodiment, distal portion 116 is connected to the implant so that distal portion 116 cannot pivot with respect to the implant. In other embodiments, distal portion may be configured to permit rotation in at least one plane with respect to the implant. Alternatively, distal portion could have other features, such as open or closed apertures, that would fit with complementary features of an implant. Distal portion 116 may also include an area having flats 127 for accommodating a holding or turning tool (not shown). Flats 127 may form a hexagon or other appropriate shape in cross-section.

Figure 26:
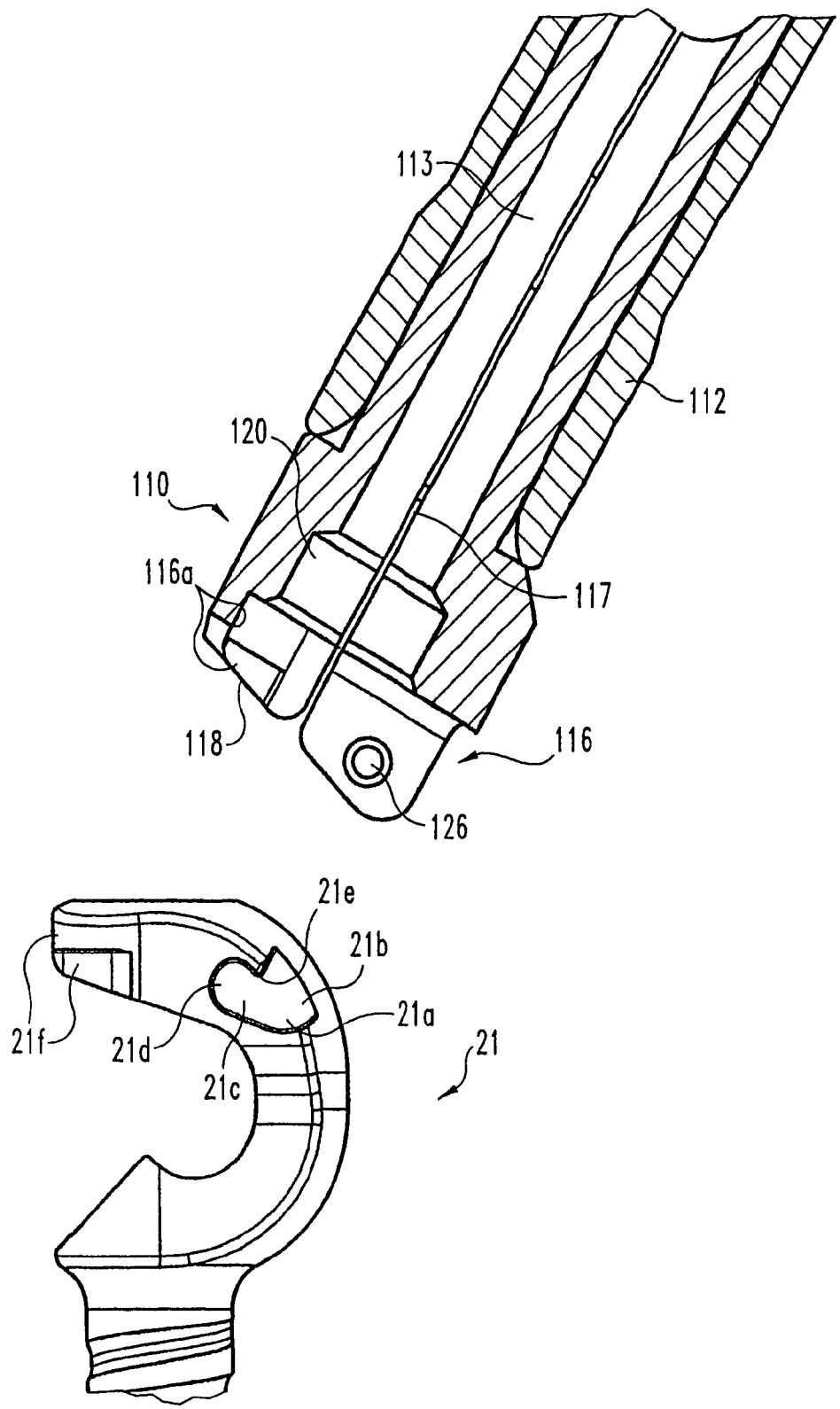
FIG. 26 is a part cross-sectional view of an embodiment of an instrument adjacent an embodiment of an implant.
Figure 27:
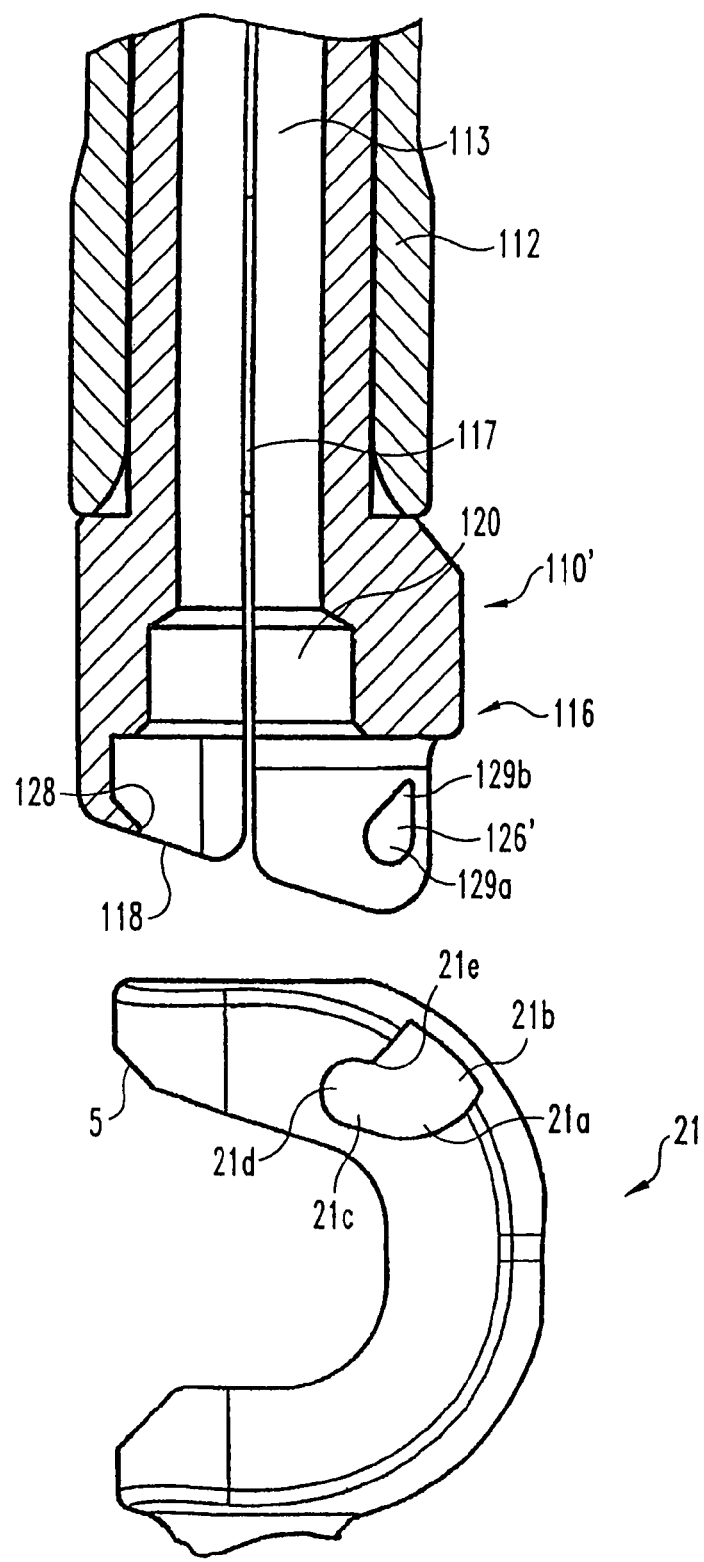
FIG. 27 is a part cross-sectional view of another embodiment of an instrument adjacent another embodiment of an implant.

Another embodiment of internal piece 110' (e.g. FIG. 27) includes many of the same or similar features as internal piece 110, and parts of internal piece 110' can be used or incorporated with internal piece 110, and vice versa. Further, the numbers used above with respect to internal piece 110 are also used to describe the same or similar features of internal piece 110'. For example, internal piece 110' includes a central lumen 113, distal portion 116, slot 117, surface 118 and chamber 120, substantially as described above. Internal piece 110' may also include an angled surface or lip 128 distal of chamber 120, and on one side of slot 117. Lip 128 in a particular embodiment is configured to abut a similarly angled surface S of an implant 21. Among the possible embodiments of implant 21 are those disclosed in U.S. patent application Ser. Nos. 11/000,585 and 11/000,846, filed Dec. 1, 2004, both of which are incorporated by reference herein in their entireties. Lip 128 may thus provide a secure contact with a front portion of implant 21, and may provide a pop-on/pop-off connection with implant 21, e.g., lip 128 may have to be forced into and out of contact with surface S of implant 21. In embodiments in which implant 21 is otherwise configured, for example having one or more rounded or slanted front surfaces (e.g. 21f in FIG. 26), inner surface(s) in distal portion 116 (e.g. 116a in FIG. 26) can be configured to abut or complement such front surfaces of an implant.

Internal piece 110' may include one or more protrusions 126' to one side of slot 117. In a particular embodiment, protrusions 126' are substantially opposite lip 128, and are substantially tear-drop shaped, having a rounded or bulbous lower portion 129a and a narrow and/or pointed upper portion 129b.

In a particular embodiment, implant 21 may include one or more indentations 21a for receiving protrusions 126 or 126', or other protrusions or features included on distal end 116 or other tool. Indentations 21a are shown in one embodiment on either side of an upper part of implant 21, but indentations 21a could be in other parts of implant 21. Indentations 21a in the illustrated embodiments have an entry portion 21b and a holding portion 21c. Holding portion 21c has a rounded or part circular portion 21d having a corner 21e. Protrusion(s) 126 or 126' may be inserted at entry portion(s) 21b and curved, angled or hooked around corner 21e into circular portion 21d. In this manner, distal portion 116 can be pivoted onto and connected to implant 21 from the side or top of implant 21, i.e. from a position not covering or impeding access to an open mouth of implant 21. Such pivoting may be limited by contact between upper portion 129b of protrusion 126' and the side of entry portion 21b of indentation 21a, or by contact between a part of distal portion 116 and the upper part of implant 21. As noted previously, distal portion 116 is relatively fixed with respect to implant 21 when connected to implant 21. In particular, in the embodiment of distal portion 116 that includes protrusions 126' and lip 128, distal portion 116 may be configured so that when connected to implant 21, lip 128 abuts surface S of implant 21, and protrusion 126' contacts or is closely adjacent to the side of indentation 21a. In that case, distal portion 116 (and the rest of instrument 20) is relatively firmly connected to implant 21, removing looseness that can occur with other devices in the connection between the instrument and the implant. In other embodiments, distal portion may be configured to allow pivotability with respect to implant 21, to provide an additional way to reduce a rod.

External piece 112, in the illustrated embodiment, is substantially tubular with a lumen 130 so that it can slide up and down around internal piece 110 between positions adjacent distal portion 116 and relatively remote from distal portion 116. When external piece 112 is relatively adjacent to distal portion 116, distal portion 116 (with slot 117) is relatively non-expandable. External piece 112 may have an inner diameter that is substantially equal to or less than an unstressed outer diameter of distal portion 116, e.g. an outer diameter measured when distal portion 116 is not being expanded or contracted. A proximal portion 131 may be formed as a grip with indentations 132 or other structure to permit the surgeon to grip or move external piece 112 as may be necessary. A distal portion 134 may have an internal print 136 that is compatible with flats 127 of internal piece 110. For example, in the embodiment in which flats 127 form a hexagonal crosssection, print 136 may be hexagonal. One or more side slots 138 may also be provided. The maximum outer diameter of the illustrated embodiment of external piece 112 is approximately equal to or slightly less than the distance between leg portions 32 and 34 of reducer portion 26.

A pin or axle 140 is provided in the illustrated embodiment. Axle 140 can link together internal piece 110 and external piece 112, as well as fitting at least partially into hollows 70 and 72 of sleeve 28 of rod adjusting assembly 22. Axle 140 is substantially cylindrical in one embodiment, with a middle groove 142. Axle 140 is positioned in hole 124 of internal piece 110 so that ends of axle 140 extend out of hole 124 and through side slots 138 of external piece 112. Axle 140 is preferably relatively firmly fixed within hole 124 so that axle 140 does not fall out. Translational sliding of external piece 112 and internal piece 110 with respect to each other is not impeded by axle 140. In an alternative embodiment to that shown, axle 140 could extend out of only one side of internal piece 110. In an embodiment in which the diameter of axle 140 is significantly less than the width of slot(s) 138, there may be some possibility of relative rotation between internal piece 110 and external piece 112. Axle 140 may be a piece separate from internal piece 110, or may be integral with one or both sides of internal piece 110. In one embodiment, axle 140 does not extend through internal piece 110.

In another embodiment, a holding assembly may be or include a forceps element 310. Forceps element 310 may include separate arms 312 pivotably connected at a point 314. Each of arms 312 include a handle portion 316 and a locking strip 318, which locking strips can interengage, as are well known in such instruments. Each of arms 312 has a distal portion or end 320, which distal portion or ends form a slotted portion made to connect to, hold or grip the head of an implant, such as a bone screw or hook. The slot of slotted portion results from the separation of the arms 312 of forceps element 310. An opening 322 may be formed in one or both of the distal portions 320, and such opening may be substantially circular. Distal portions 320 may include protrusions 323 extending into or adjacent to opening 322. Spreading handle portions 316 from each other results in spreading of distal portions 320 from each other. Closing handle portions 316 toward each other results in closing of distal portions 320 toward each other, and in connection of distal portions 320 with an implant head. Forceps element 310 further includes an axle 324, which in the illustrated embodiment is in two parts each fixed to or integral with an arm 312, i.e. axle 324 does not go through either of arms 312. Alternative embodiments could include an axle that is not integral with or fixed to one or both arms 312, and/or an axle extending from only one arm 312. Axle 324 is connectible to embodiments of rod adjusting assembly (e.g. assembly 24 described above) in substantially the same manner as described above for axle 140 of internal piece 110.

Figure 36:
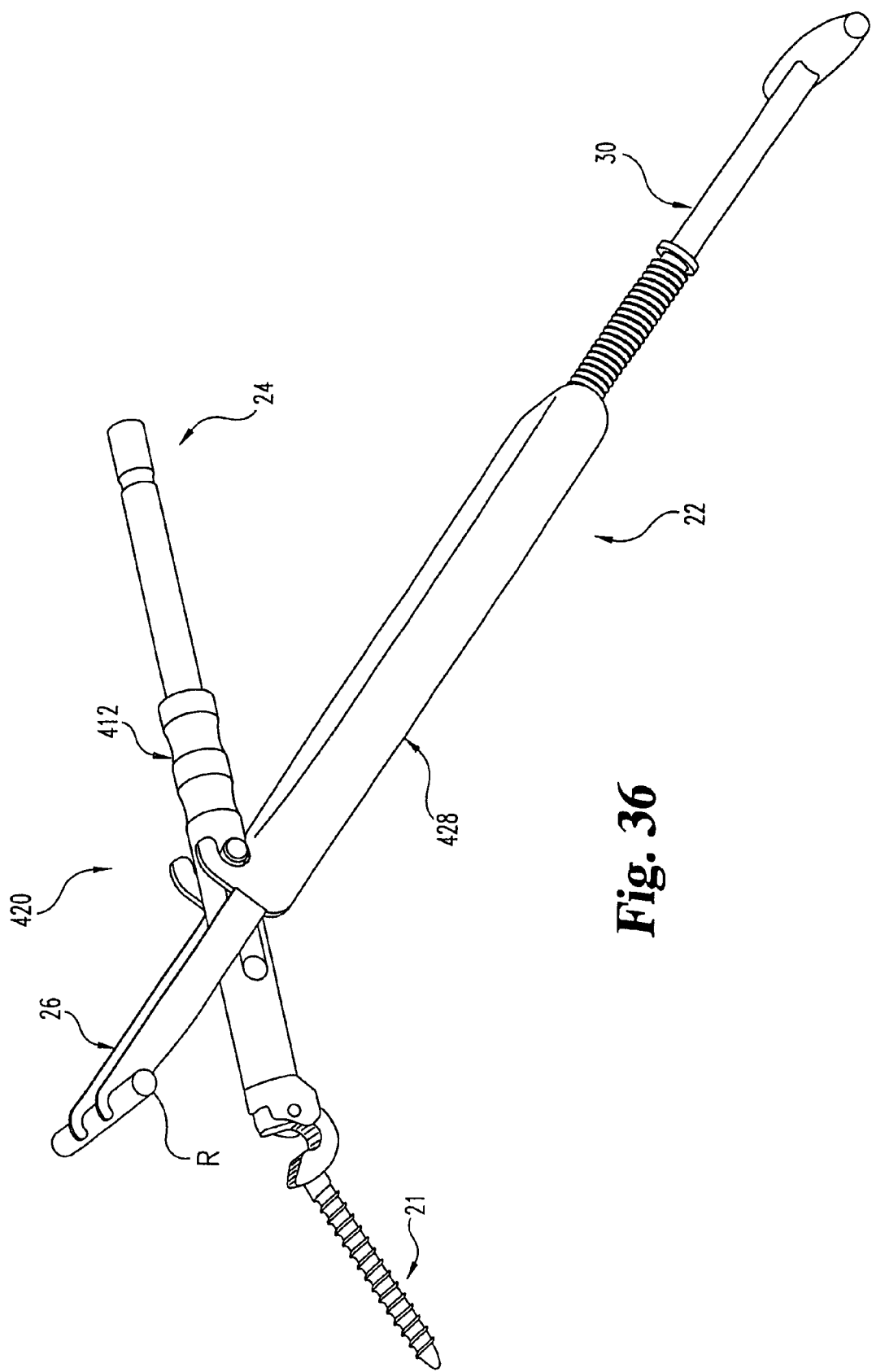
FIG. 36 is a perspective view of an alternative embodiment of an instrument for reducing a rod into an orthopedic implant.

An alternative embodiment of instrument 420 is shown in FIG. 36. That embodiment shows a sleeve element 428 that is substantially linear in configuration, rather than angled as in the embodiment described above. External part 412 has a different external shape than the embodiment described above. In other respects, instrument 420 is substantially the same as instrument 20.

Rod adjusting assembly 22 and implant holding assembly 24 are connected together. Further description of assembly and use will refer to instrument 20, assembly 22 and assembly 24. It will be understood that other embodiments are assembled and used in similar or identical fasion. In a particular embodiment, portions of axle 140 that extend on either side of implant holding assembly 24 are fitted into hollows 70 and 72 of sleeve 28 of rod adjusting assembly 22. In embodiments having plunger(s) 76 in one or both of hollows 70 and 72, such plunger(s) 76 assist in retaining axle 140 within hollows 70 and/or 72. Axle 140 is held between the surface of a hollow and a ball 80 of a plunger 76.

In using the illustrated embodiment of instrument 20, it will be seen that a variety of motions are possible. Turning adjustment mechanism 30 moves hollows 42 and 44 of reducer portion 26 (which can accommodate an orthopedic rod R or other elongated member) toward or away from implant holding assembly 24. Rod adjusting assembly 22 can be rotated about axle 140 with respect to implant holding assembly 24. As noted above, in certain embodiments instrument 20 can be rotated about the head of implant 21. One or more of these motions can be used to insert rod R into implant 21.

The operation of instrument 20 to engage an implant and rod or other connecting member and seat the connecting member in the implant anchor will now be described with respect to operation on a spinal column. Alternative uses with respect to other bony structures or other tissues can be made. As with other types of orthopedic surgery, an incision is made and access is gained to the surgical site. The approach to the surgical site can be an open approach, i.e. a relatively long incision with retraction of underlying tissue. The instrument disclosed herein can be used in such an approach, or with other surgical techniques.

After access to the surgical site has been obtained, anchors such as implant 21 including a receiving portion 150 with a side-facing mouth 152 are inserted into bone tissue. Such anchors may be pre-fitted with such a receiving portion or other receiver embodiment, and such anchors typically include a bone engaging portion and a channel for accommodating part of connecting member R. Such receiver members may also be placed on or over bone engaging portion(s) after engagement of such portion(s) into bone. Receiving portion 150, in other embodiments, can be multi-axial, pivotable or otherwise adjustable with respect to its bone engaging portion. A connecting member, e.g. a spinal rod R, is inserted into the surgical site, and placed adjacent one or more of the anchors. If not already present, anchors and/or receiving portions of anchors may be loosely placed on the connecting member prior to insertion of the connecting member to the surgical site. The anchors and connecting member are manipulated so that a part of the connecting member is in or near the each of the anchors.

Implant 21 is engaged to the spinal column so that it can receive and engage a rod or other elongate connecting member along the spinal column. Instrument 20 may be used with a variety of anchors or implants, including those known previously in the art and those disclosed in U.S. patent application Ser. Nos. 11/000,585 and 11/000,846, respectively entitled SIDE-LOADING ADJUSTABLE BONE ANCHOR and SIDE-LOADING BONE ANCHOR, both filed on Dec. 1, 2004, which are incorporated herein by reference in their entireties. Instrument 20 may have particular application with side-loading implants.

After engagement of implant(s) 21 to a vertebra, rod R is positioned adjacent the implant. It is contemplated that a number of implants can be positioned and engaged along the spinal column, and the rod engaged in a channel or other area of one of the implants. Due to misalignment of vertebrae, misalignment of the implants, or other conditions, the rod may not be easily or readily positioned in one or more implants.

Once rod R is adjacent implant 21 into which the rod is to be placed or seated, instrument 20 may be introduced to reduce or force rod R into implant 21. Rod R is connected to rod adjustment assembly 22 by fitting or snapping into hollows 42 and 44 of reducer portion 26. To attach implant holding assembly 24 to implant 21, external piece 112 is slid up toward proximal portion 114 of internal piece 110. Distal portion 116 of internal piece 110 is placed over implant 21 so that protrusions 126 are within or adjacent to complementary openings in implant 21, an embodiment of which placement is described above. This discussion uses internal piece 110 and its features described above for simplicity, it being understood as applicable to internal piece 110' and its features described above as well. External piece 112 is slid down toward distal portion 116 of internal piece 110. In embodiments in which internal piece 110 includes flats 127 and external piece 112 includes print 136, those features may abut or be adjacent each other. External piece 112, when slid down toward distal portion 116 of internal piece 110, inhibits distal portion 116 from expanding and thus tends to maintain the relationship between distal portion 116 and implant 21. In certain embodiments, the inside of external piece 112 (e.g. print 136) may be sized so as to exert some pressure on an outside portion of internal piece 110 (e.g. flats 127), so that distal portion is pressed toward or against a portion of implant 21.

As noted above, one or more of the motions instrument 20 allows can be used for reduction of the rod. If rod R is relatively close to the mouth of implant 21, and an embodiment in which assembly 24 is pivotable with respect to implant 21, it may only be necessary to pivot implant holding assembly 24 with respect to implant 21, without moving rod adjusting assembly 22 appreciably. With reference to FIG. 36, if assembly 424 is rotated counter-clockwise, rod R moves toward the mouth of implant 21.

After connecting rod R to reducer portion 26, handle 98 of adjustment mechanism 30 can be turned to move rod R with respect to implant 21, e.g. relatively toward implant 21 and sleeve 28. Turning handle 98, as indicated above, results in threaded portion 100 of adjustment mechanism 30 moving with respect to threaded portion 92 of button 88. Adjustment mechanism 30 thus moves outwardly with respect to button 88 and sleeve 28, pulling reducer portion 26 and causing it to slide further within sleeve 28. Following such movement, rod adjusting assembly 22 can be pivoted around axle 140 with respect to implant holding assembly 24. With such pivoting, rod R may be forced toward and into the mouth of implant 21. Additional minor adjustments can be made as described above by pivoting implant holding assembly 24 about implant 21. It will be seen that large and small changes in rod position with respect to an implant can be accomplished by rotating handle 98 so that reducer portion 26 (and rod R) moves toward or away from sleeve 28, and/or by rotating rod adjusting assembly 22 with respect to implant holding assembly 24.

Similarly, in embodiments having internal piece 110', protrusion(s) 126' and/or lip 128, in which internal piece 110' is relatively non-pivotable with respect to implant 21 when securely connected to it, in that case rod R will be reduced through the action of rotating handle 98 to move reducer portion 26 and rod R relative to sleeve 28 and implant holding assembly 24, and/or by rotating rod adjusting assembly 22 with respect to implant holding assembly 24. For example, handle 98 can be rotated to bring rod R closer to implant holding assembly 24. When rod R is in a desired position, then rod adjusting assembly 22 can be rotated to force rod R into implant 21.

Rod R should be reduced or forced into implant 21 until it is in a position where it will remain within implant 21 when locked. Once rod R is in a desired position with respect to implant 21, a locking mechanism, such as a set screw, clamp, cap, or other device provided with the implant, is attached to implant 21 and applied directly or indirectly to rod R to retain rod R within implant 21. In embodiments using a set screw to be threaded into the top of implant 21, such a set screw can be held or placed within internal piece 110 of implant holding assembly 24, e.g. within chamber 120. When implant holding assembly 24 is connected to implant 21, the set screw is adjacent such threaded top of implant 21. Once sufficient rod reduction has occurred, a screwdriver may be advanced through lumen 113 of internal piece 110 of implant holding assembly 24 and into contact with the set screw. Manipulating the screwdriver causes the set screw to be threaded into implant 21 to lock rod R therein. In this embodiment, it is therefore not necessary to remove the reducing instrument 20 before locking rod R within implant 21.

The anchors and connecting member may be positioned in or along one or more parts of the spine, including the cervical, thoracic, lumbar and/or sacral portions. Although the use of instrument 20 is described in the above context, instrument 20 could be used with a variety of screws, hooks or other fixation implants, or in connection with orthopedic implants in parts of the body other than the spine.

The above embodiment may be made of stainless steel, certain hard plastics, or other materials that are compatible with surgical procedures and the implants and rods with which instrument 20 is used.

An assembly for holding an implant head need not include an external part, as described in the embodiment above, but may include only a single part such as internal piece 110 or forceps element 310.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. An apparatus for rod reduction, comprising:
   a first assembly having a slotted distal portion adapted to connect to an orthopedic implant head and an axle in a middle portion;
   a second assembly pivotably connected to said first assembly, said second assembly including a substantially U-shaped reducer portion having at least one hollow into which an orthopedic rod may be placed, a substantially U-shaped sleeve portion within which said reducer portion is slidable and having at least one hollow into which said axle may be placed, and an adjustment mechanism including a rotatable threaded shaft extending through said sleeve portion and connected to said reducer portion, whereby turning said threaded shaft causes said reducer portion to slide along said sleeve portion; and
   wherein said first assembly includes an inner piece and an outer piece and said slotted distal portion of said first assembly is positioned on said inner piece and includes a plurality of flat surfaces;
   wherein said outer piece of said first assembly includes a lumen therethrough and said outer piece is slideably placed around said inner piece, and wherein said outer piece includes a plurality of flat surfaces within said lumen that are complementary with said flat surfaces of said inner piece; and
   wherein sliding said outer piece toward said distal end of said inner piece causes said flat surfaces of said outer piece to contact said flat surfaces of said inner piece on that pressure is exerted on said flat surfaces of said inner piece, whereby said slotted distal end is forced together.

2. The apparatus of claim 1, wherein said outer piece has at least one slot through which said axle extends.

3. The apparatus of claim 1, wherein said first assembly is a forceps having a handle portion connected to said slotted distal portion, said slotted distal portion adapted to clamp around the orthopedic implant head.

4. The apparatus of claim 1, further comprising a button having a pressing surface and an elongated hole that is at least partially threaded on a surface relatively distal from said pressing surface, said button being operatively connected to said sleeve portion so that said threaded shaft extends through said elongated hole, said button being biased such that said threaded portion of said elongated hole normally engages the thread on said threaded shaft, and pressing said button disengages said threaded portion of said elongated hole from said threaded shaft.

5. The apparatus of claim 1 wherein said slotted distal portion includes at least one protrusion adapted to be placed at least partially within a portion of said head of said implant, and said first assembly is pivotable about said head.

6. An apparatus for rod reduction, comprising:
a first assembly having a slotted distal portion adapted to connect to an orthopedic implant head and an axle in a middle portion;
a second assembly pivotably connected to said first assembly, said second assembly including a substantially U-shaped reducer portion having at least one hollow into which an orthopedic rod may be placed, a substantially U-shaped sleeve portion within which said reducer portion is slidable and having at least one hollow into which said axle may be placed, and an adjustment mechanism including a rotatable threaded shaft extending through said sleeve portion and connected to said reducer portion, whereby turning said threaded shaft causes said reducer portion to slide along said sleeve portion;
wherein said hollow of said sleeve portion includes a hole, and further comprising a spring-loaded ball placed within said hole, wherein said axle is maintained within said hollow of said sleeve portion through contact with said ball.

7. An apparatus for rod reduction, comprising:
a first assembly having a slotted distal portion adapted to connect to an orthopedic implant head and an axle in a middle portion;
a second assembly pivotably connected to said first assembly, said second assembly including a substantially U-shaped reducer portion having at least one hollow into which an orthopedic rod may be placed, a substantially U-shaped sleeve portion within which said reducer portion is slidable and having at least one hollow into which said axle may be placed, and an adjustment mechanism including a rotatable threaded shaft extending through said sleeve portion and connected to said reducer portion, whereby turning said threaded shaft causes said reducer portion to slide along said sleeve portion;
wherein said sleeve portion includes a pair of legs, each of said having an upper portion and a lower portion, said upper portions being substantially parallel to each other, and said lower portions being substantially parallel to each other, and each lower portion being angled with respect to its respective upper portion.

8. The apparatus of claim 7, wherein said first assembly includes an inner piece and an outer piece and said slotted distal portion of said first assembly is positioned on said inner piece and includes a plurality of flat surfaces.

9. The apparatus of claim 8, wherein said outer piece of said first assembly includes a lumen therethrough and said outer piece is slideably placed around said inner piece, and wherein said outer piece includes a plurality of flat surfaces within said lumen that are complementary with said flat surfaces of said inner piece.

10. The apparatus of claim 7, wherein the angle between said lower portions and their respective upper portions is about 135 degrees.

11. An apparatus for rod reduction, comprising:
a first assembly having a slotted distal portion adapted to connect to an orthopedic implant head and an axle in a middle portion;
a second assembly pivotably connected to said first assembly, said second assembly including a substantially U-shaped reducer portion having at least one hollow into which an orthopedic rod may be placed, a substantially U-shaped sleeve portion within which said reducer portion is slidable and having at least one hollow into which said axle may be placed, and an adjustment mechanism including a rotatable threaded shaft extending through said sleeve portion and connected to said reducer portion, whereby turning said threaded shaft causes said reducer portion to slide along said sleeve portion;
wherein said first assembly includes an inner piece and an outer piece and said inner piece has a lumen therethrough, and a chamber concentric with and larger than a portion of said lumen formed at or adjacent to said distal portion of said inner piece.

12. The apparatus of claim 11, wherein said chamber is sized and configured to accommodate at least a portion of a set screw used in conjunction with said orthopedic implant head.

13. The apparatus of claim 12, wherein said lumen permits engagement of a set screw at least partially within said chamber by a tool for engaging said set screw with said implant head.

14. An apparatus for reducing an orthopedic rod into an implant having a head, comprising:
a first elongated element including an elongated shaft extending between a proximal end and a distal, expandable end, said expandable end sized for fitting around at least a portion of said head and said elongated shaft including an axle positioned between said proximal and distal ends;
a second elongated element having a longitudinal axis pivotably connected to said axle of said elongated shaft of said first elongated element, said second elongated element having at least one substantially U-shaped hollow for accommodating a portion of said rod, said hollow being movable with respect to said first elongated element substantially along said longitudinal axis, wherein by at least one of (1) pivoting said second elongated element with respect to said first elongated element and (2) moving said hollow along said longitudinal axis said rod is moved toward or into said head of said implant; and
a sleeve element within which said second elongated element is slidable, and an adjustment element having a handle and a threaded shaft, said threaded shaft extending through said sleeve element and into rotatable contact with said second elongated element, whereby turning said handle causes said second elongated element to slide within said sleeve element.

15. The apparatus of claim 14, wherein said first elongated element has a lumen therethrough, and a chamber concentric with and larger than said lumen formed at or adjacent to said distal portion of said inner piece.

16. The apparatus of claim 15, wherein said chamber is sized and configured to accommodate at least a portion of a set screw used in conjunction with said head.

17. The apparatus of claim 14, further comprising a button having a pressing surface and an elongated hole that is at least partially threaded on a surface relatively distal from said pressing surface, said button being operatively connected to said sleeve portion so that said threaded shaft extends through said elongated hole, said button being biased such that said threaded portion of said elongated hole normally engages the thread on said threaded shaft, and pressing said button disengages said threaded portion of said elongated hole from said threaded shaft.

18. The apparatus of claim 14, wherein said first elongated element is pivotable with respect to said head when fitted around at least a portion of said head, and wherein by at least one of (1) pivoting said second elongated element with respect to said first elongated element, (2) moving said hollow along said longitudinal axis, and (3) pivoting said first elongated element with respect to said head, said rod is moved toward or into said head of said implant.

19. A rod-reducing apparatus comprising:
 a first elongated element having a pair of spaced apart legs and a base portion such that said first elongated element is substantially U-shaped, said legs each having a proximal portion adjacent said base portion and a distal portion, said proximal portions of said legs being substantially parallel with each other, said distal portions of said legs being substantially in the same plane and angled with respect to their respective proximal portions, said distal portions each including a substantially part-cylindrical hollow, said hollows being substantially coaxial, and further including at least one spring-biased plunger in at least one of said hollows;
 a second elongated element having a pair of spaced apart legs and a base portion such that said second elongated element is substantially U-shaped, said legs each having a distal portion, said distal portions each including a substantially part-cylindrical hollow, said hollows being substantially coaxial and having a radius equal to or larger than the radius of a spinal rod, said second elongated element being slidable within said legs of said first elongated element;
 a handle assembly including a handle portion and a shaft portion connected to said handle portion, said shaft portion having a threaded portion and a groove adjacent a distal end of said shaft portion, said distal end of said shaft being connected to said base of said second elongated member, said threaded portion of said shaft extending through said base of said first elongated member;
 a substantially cylindrical button having a longitudinal axis, a pressing surface and a hole substantially perpendicular to said axis, said hole having a diameter larger than said shaft portion, said hole having a portion relatively distant from said pressing surface that is partially threaded and engageable with said threaded portion of said shaft portion; and
 wherein said button is biased relatively outward from said second elongated member so that said partially threaded portion of said hole through said button engages the threaded portion of said shaft portion when said button is not being pushed,
 whereby turning said handle assembly causes said second elongated member to slide within said first elongated member, and pushing said button disengages said button from said threaded portion of said shaft portion and enables said handle assembly and said second elongated member to move freely with respect to said first elongated member.

20. The apparatus of claim 19, wherein said first elongated element is an outer sleeve element and said second elongated element is a reducer portion.

21. The apparatus of claim 19, further comprising an assembly for connecting to an orthopedic implant head, said connecting assembly having an inner piece with a slotted distal portion adapted to pivotably connect to the orthopedic implant head and a middle portion, an axle in said middle portion, and an outer piece slideably connected to said inner piece and having at least one slot through which said axle extends, said connecting assembly being pivotably connected to said first elongated element.

22. The apparatus of claim 21, wherein said axle is at least partially within at least one of said hollows of said first elongated element.

23. The apparatus of claim 21, wherein said slotted distal portion of said inner piece includes a plurality of flat surfaces.

24. The apparatus of claim 23, wherein said outer piece includes a lumen therethrough and said outer piece is slideably placed around said inner piece, and wherein said outer piece includes a plurality of flat surfaces within said lumen that are complementary with said flat surfaces of said inner piece.

25. The apparatus of claim 24, wherein sliding said outer piece toward said distal end of said inner piece causes said flat surfaces of said outer piece to contact said flat surfaces of said inner piece so that pressure is exerted on said flat surfaces of said inner piece, whereby said slotted distal end is forced together.

26. The apparatus of claim 21 wherein said slotted distal portion includes at least one protrusion adapted to be placed at least partially within a portion of said head of said implant, whereby the apparatus is pivotable about said head.

27. The apparatus of claim 21, wherein said inner piece has a lumen therethrough, and a chamber concentric with and larger than said lumen formed at or adjacent to said distal portion of said inner piece.

28. The apparatus of claim 27, wherein said chamber is sized and configured to accommodate at least a portion of a set screw used in conjunction with the orthopedic implant head.

29. The apparatus of claim 19, wherein the angle between said distal portions of said legs of said first elongated element and their respective proximal portions is about 135 degrees.

* * * * *

UNITED STATES PATENT AND TRADEMARK OFFICE
CERTIFICATE OF CORRECTION

PATENT NO. : 7,799,031 B2  Page 1 of 1
APPLICATION NO. : 11/701979
DATED : September 21, 2010
INVENTOR(S) : Miller et al.

It is certified that error appears in the above-identified patent and that said Letters Patent is hereby corrected as shown below:

In Column 10, Line 61, in Claim 1, delete "on" and insert -- so --, therefor.

In Column 11, Line 53, in Claim 7, before "having" insert -- legs --.

Signed and Sealed this
Third Day of May, 2011

David J. Kappos
*Director of the United States Patent and Trademark Office*